United States Patent [19]
Breton et al.

[11] Patent Number: 5,900,257
[45] Date of Patent: May 5, 1999

[54] COSMETIC/PHARMACEUTICAL COMPOSITIONS COMPRISING LANTHANIDE MANGANESE, TIN AND/OR YTTRIUM SALTS AS SUBSTANCE P ANTAGONISTS

[75] Inventors: Lionel Breton, Versilles; Olivier De Lacharriere, Paris, both of France

[73] Assignee: Societe L'Oreal S.A., Paris, France

[21] Appl. No.: 08/738,811

[22] Filed: Oct. 28, 1996

[30] Foreign Application Priority Data

Oct. 26, 1995 [FR] France .................................. 95-12658

[51] Int. Cl.$^6$ ..................................................... A61K 33/32
[52] U.S. Cl. .......................... 424/639; 424/600; 424/617; 424/646; 424/650; 424/677; 424/715; 424/718; 424/722
[58] Field of Search ..................................... 424/722, 600, 424/617, 639, 646, 650, 677, 715, 718

[56] References Cited

U.S. PATENT DOCUMENTS

| | | | |
|---|---|---|---|
| 3,519,711 | 7/1970 | Svigals | 424/659 |
| 3,772,431 | 11/1973 | Mlkvy et al. | 424/44 |
| 3,888,976 | 6/1975 | Mlkvy et al. | 424/44 |
| 4,477,439 | 10/1984 | D'Alelio | 424/604 |
| 4,735,802 | 4/1988 | Le | 424/682 |
| 4,938,969 | 7/1990 | Schinitsky et al. | 424/642 |
| 4,943,432 | 7/1990 | Biener | 424/647 |
| 4,980,184 | 12/1990 | Gordon | 426/335 |
| 4,986,981 | 1/1991 | Glace et al. | 424/50 |
| 5,047,409 | 9/1991 | Di Schiena et al. | 514/275 |
| 5,079,010 | 1/1992 | Natterer | 424/617 |
| 5,091,171 | 2/1992 | Yu et al. | 424/642 |
| 5,202,130 | 4/1993 | Grant et al. | 424/617 |
| 5,296,476 | 3/1994 | Henderson | 514/574 |
| 5,401,730 | 3/1995 | Sauvage et al. | 514/165 |
| 5,716,625 | 2/1998 | Hahn et al. | 424/401 |

FOREIGN PATENT DOCUMENTS

| | | |
|---|---|---|
| 0085579 | 8/1983 | European Pat. Off. . |
| 0135312 | 3/1985 | European Pat. Off. . |
| 0217975 | 4/1987 | European Pat. Off. . |
| 0 401 503 | 4/1990 | European Pat. Off. . |
| 0409662 | 1/1991 | European Pat. Off. . |
| 0439640 | 8/1991 | European Pat. Off. . |
| 0451300 | 10/1991 | European Pat. Off. . |
| 045890 | 12/1991 | European Pat. Off. . |
| 0 522 808 | 7/1992 | European Pat. Off. . |
| 0586929 | 3/1994 | European Pat. Off. . |
| 5394 | 10/1967 | France . |
| 2122613 | 9/1972 | France . |
| 2184890 | 6/1978 | France . |
| 3338957 | 5/1985 | Germany . |
| 0280692 | 7/1990 | Germany . |
| 0297062 | 1/1992 | Germany . |
| 4315866 | 5/1994 | Germany . |
| 1072355 | 6/1964 | United Kingdom . |
| 2217602 | 11/1989 | United Kingdom . |
| 2271774 | 4/1994 | United Kingdom . |
| WO 83/01252 | 4/1983 | WIPO . |
| WO87/01935 | 10/1986 | WIPO . |
| WO93/01165 | 7/1992 | WIPO . |
| WO 93/14084 | 7/1993 | WIPO . |
| 91/02130 | 2/1994 | WIPO . |
| 94/09798 | 5/1994 | WIPO . |
| WO 96/19184 | 6/1996 | WIPO . |

*Primary Examiner*—Shelley A. Dodson
*Assistant Examiner*—Michael A. Williamson
*Attorney, Agent, or Firm*—Burns, Doane, Swecker & Mathis, L.L.P.

[57] ABSTRACT

Cosmetic/dermatological/pharmaceutical compositions, well suited for the treatment of a variety of mammalian disorders of, for example, the skin, hair and/or mucous membranes, a manifestation of which is an excess in the synthesis and/or in the release of substance P, e.g., for the treatment of cutaneous disorders and sensitive skin, comprise an effective substance P antagonist amount of at least one salt of yttrium, lanthanum, cerium, praseodymium, neodymium, promethium, samarium, europium, gadolinium, terbium, dysprosium, holmium, erbium, thulium, ytterbium, lutetium, tin, manganese, or mixture thereof, in a cosmetically/pharmaceutically acceptable medium therefor.

19 Claims, No Drawings

COSMETIC/PHARMACEUTICAL COMPOSITIONS COMPRISING LANTHANIDE MANGANESE, TIN AND/OR YTTRIUM SALTS AS SUBSTANCE P ANTAGONISTS

BACKGROUND OF THE INVENTION

1. Technical Field of the Invention

The present invention relates to novel cosmetic, dermatological or pharmaceutical compositions comprising at least one lanthanide, manganese, tin or yttrium salt as a substance P antagonist, for the treatment of disorders associated with an excessive synthesis and/or release of substance P and, more especially, for the treatment of sensitive skins.

2. Description of the Prior Art

Polypeptides belonging to the tachykinin family exist in mammals which induce rapid contractions of the smooth muscle fibers. Exemplary compounds of this family include β-neurokinin, α-neurokinin and substance P.

Substance P is a polypeptide chemical species (undecapeptide), produced and released by a nerve ending. The location of substance P is specific to the neurons, both in the central nervous system and in the organs at the periphery. Thus, very many organs or tissues receive afferences of substance P neurons; these are especially the salivary glands, stomach, pancreas, intestine (in the latter, the distribution of substance B is superposed on the intrinsic Meissner and Auerbach nervous plexus), cardiovascular system, thyroid gland, skin, iris and ciliary bodies, bladder and, obviously, the central and peripheral nervous systems.

By virtue of the ubiquitous distribution of substance P, very many disorders are associated with an excessive synthesis and/or release of substance P.

Substance P is involved, in particular, in the transmission of pain (dental, cutaneous, tympanic) and in diseases of the central nervous system (for example anxiety, psychoses, neuropathies, neurodegenerative disorders of the Alzheimer senile dementia type, dementia in Aids patients, Parkinson's disease, Down's syndrome, Korsakoff's syndrome, multiple scleroses, schizophrenia, psychotic diseases), in respiratory diseases (such as, for example, bronchial pneumonia, cough, emphysema, bronchiolitis) and inflammatory diseases (such as, for example, rheumatoid arthritis), in allergic syndromes (for example asthma, allergic rhinitis, allergic pharyngitis, urticaria, eczematous dermatitis), in gastrointestinal diseases (such as, for example, ulcers, colitis, Crohn's disease, gastritis, gastroenteritis, intestinal spasticities), in skin disorders (such as, for example, psoriasis, prurigenous diseases, herpes, photodermatosis, atopic dermatitis, contact dermatitis, lichens, prurigos, pruritus, rosacea, ulcers, zona, demodicidoses, acne rosacea, sensitive skins, dartres, solar and emotional erythemas, insect burns), in fibroses and other collagen maturation disorders (such as, for example, scleroderma), in cardiovascular diseases, vasospastic disorders (such as, for example, migraine, Raynaud's disease), in immunological disorders, in disorders of the urinary or genital tract (such as, for example, incontinence, cystitis), in rheumatic diseases, in certain dermatological diseases (such as eczema) and in ophthalmological conditions (such as, for example, conjunctivitis, uveitis, ocular pruritus, blepharitis, irritations and ocular pain).

The administration of a substance P antagonist is one of the therapeutic alternatives which are effective in all of the conditions and afflictions indicated above.

By "substance P antagonist" is intended any compound or species capable of partially, or even completely inhibiting the biological effect of substance P. In particular, for a substance to be recognized as a substance P antagonist, it must induce a coherent pharmacological response (including or otherwise its binding to the substance P receptor), in particular in one of the following tests:

(a) the antagonist substance must reduce the extravasation of the plasma across the vascular wall induced by capsaicin or by an antidromic nerve stimulation, or, alternatively;

(b) the antagonist substance must cause inhibition of the contraction of the smooth muscles induced by the administration of substance P.

To date, substance P antagonists have been administered to treat the disorders indicated above.

SUMMARY OF THE INVENTION

It has now unexpectedly and surprisingly been determined that lanthanide, manganese, yttrium and tin salts exhibit substance P antagonizing activity as defined above and therefore are useful for treating the disorders indicated above.

Thus, the present invention features the administration of at least one lanthanide, manganese, tin or yttrium salt as a substance P antagonist in a cosmetic/pharmaceutical composition.

This invention also features cosmetic/dermatological/pharmaceutical compositions comprising at least one salt of a lanthanide, manganese, tin and/or yttrium, or mixture thereof, for the treatment of disorders associated with an excessive synthesis and/or release of substance P.

DETAILED DESCRIPTION OF BEST MODE AND SPECIFIC/PREFERRED EMBODIMENTS OF THE INVENTION

More particularly according to the present invention, by "lanthanide" are intended the elements of atomic number z ranging from 57 to 71, namely, lanthanum, cerium, praseodymium, neodymium, promethium, samarium, europium, gadolinium, terbium, dysprosium, holmium, erbium, thulium, ytterbium, and lutetium.

The present invention is applicable to all of the disorders associated with an excessive synthesis and/or release of substance P that are mentioned above.

Thus, in a preferred embodiment of the invention, at least one lanthanide, manganese, tin or yttrium salt is formulated into a cosmetic or dermatological or pharmaceutical composition for the treatment of disorders of the central nervous system, respiratory disorders, allergic syndromes, inflammation, pain, gastrointestinal disorders, skin disorders, fibrosis, collagen maturation disorders, cardiovascular disorders, vasospastic disorders, immunological disorders, as well as disorders of the urinogenital tract, ophthalmic and pancreatic disorders.

In the field of skin or cutaneous disorders, it is known that certain skins are more sensitive than others. However, the symptoms of sensitive skins were, until now, poorly characterized and the problem of these skins was, as a result, poorly defined. Indeed, the process implicated in skin sensitivity was not exactly known. Some thought that a sensitive skin was a skin which reacted to cosmetic products, others that it was a skin which reacted to several external factors, not necessarily linked to cosmetic products. Sensitive skins were also classified as allergic skins.

Tests have been developed to assess sensitive skins, for example tests based on lactic acid and DMSO, which are known to be irritant substances: see, for example, the article by K. Lammintausta et al, *Dermatoses*, 36, pages 45–49 (1988); and the article by T. Agner and J. Serup, *Clinical and Experimental Dermatology*, 14, pages 214–217 (1989).

Because of the lack of knowledge as to the characteristics of sensitive skins, it was, until now, very difficult or even impossible to treat them. Indeed, they were treated indirectly, for example by limiting the employment, in cosmetic or dermatological compositions, of products of an irritant nature, such as surfactants, preservatives or perfumes, as well as the employment of certain cosmetic or dermatological active agents.

After numerous clinical tests, the symptoms related to sensitive skins have now been determined. These symptoms are in particular subjective signs, which are essentially dysaesthetic sensations. By "dysaesthetic sensations" are intended sensations painful to a greater or lesser extent, which are experienced in a skin area, such as pricking or pins and needles, smarting, itching or pruritus, burning sensations, inflammation, discomfort, stabbing pain and the like.

The assignee hereof has been able to demonstrate, in addition, that a sensitive skin was not an allergic skin. Indeed, an allergic skin is a skin which reacts to an external agent, an allergen, which triggers an allergic reaction. It is an immunological cascade which occurs only when an allergen is present and which only affects sensitized subjects. The essential characteristic of sensitive skin is, again according to the assignee hereof, on the contrary, a mechanism of response to external factors, which may affect any individual, even if the so-called individuals with sensitive skin react more quickly thereto than others. This mechanism is not immunological; it is aspecific.

Thus, it has been found that sensitive skins could be divided into two main clinical forms, irritable and/or reactive skins, and intolerant skins.

An irritable and/or reactive skin is a skin which reacts through a pruritus, namely, through itching or through pricking, to various factors such as the environment, emotion, food, the wind, rubbing, shaving, soap, surfactants, hard water with a high concentration of calcium, temperature variations or wool. In general, these signs are associated with a dry skin with or without sores, or with a skin having an erythema.

An intolerant skin is a skin which reacts, through sensations of warming inflammation, stabbing pain, pins and needles and/or reddening, to various factors such as the environment, emotions, food and certain cosmetic or dermatological products or soaps. In general, these signs are associated with a hyperseborrhoeic or acne-prone skin, or even rosacea-like skin with or without sores, and with an erythema.

"Sensitive" scalps have a more univocal clinical semiology: sensations of pruritus and/or pricking and/or inflammation are essentially triggered by local factors such as rubbing, soap, surfactants, hard water with a high concentration of calcium, shampoos or lotions. These sensations are also sometimes triggered by factors such as the environment, emotion and/or food or cosmetic or dermatological products. An erythema and a hyperseborrhoea of the scalp as well as a dandruff condition, are frequently associated with the above signs.

Moreover, in certain anatomical regions, such as the major skin-folds (inguinal, genital, axillary, popliteal, anal, or submammary regions, skin-folds of the elbow) and the feet, sensitive skin is reflected by pruriginous sensations and/or dysaesthetic sensations (inflammation, pricking) related in particular to sweat, rubbing or friction, wool, surfactants, certain cosmetic preparations, hard water with a high concentration of calcium and/or temperature variations.

To determine if a skin is sensitive or not, the assignee hereof has also developed a test. Indeed, after having carried out a great number of tests with the aim of defining a sensitive skin, it has been found, surprisingly, that there existed a connection between individuals with sensitive skin and those who reacted to a topical application of capsaicin.

The capsaicin-based test entails topically applying to about 4 $cm^2$ of skin 0.05 ml of a cream comprising 0.075% capsaicin and in noting the appearance of subjective signs caused by this application, such as pricking, smarting, burning sensations and itching. In subjects with sensitive skins, these signs appear between 3 and 20 minutes after application and are followed by the appearance of an erythema which starts at the periphery of the area of application.

To date, capsaicin has been used as a medicinal product, in particular for treating zona pain and shingles. Capsaicin causes release of the neuropeptides, and in particular of the tachykinins which emanates from nerve endings of the epidermis and of the dermis. It has been found that the physiopathological pattern common to all of the states of sensitive skins was related to a great ability to release tachykinins and more particularly substance P in the skin. The dysaesthetic manifestations which are caused by their release are termed "neurogenic".

The clinical signs of sensitive skin are essentially subjective: pins and needles or pricking, burning sensation, pruritus, stabbing pain and inflammation, and are sometimes associated with erythemas. These signs are due to aspecific external factors. The symptoms appear to be essentially localized to the face, the neck and the scalp, but may also appear anywhere on the body.

Thus, it has now been determined that one of the essential characteristics of sensitive skins is related to the release and/or synthesis of substance P and therefore that the use of substance P antagonists can make it possible to obtain a preventive and/or curative effect for sensitive skins.

To treat sensitive skins, substance P antagonists are administered. Indeed, it has surprisingly been found that the incorporation of a substance P antagonist into a composition intended for topical application prevents irritation and/or dysaesthetic sensations and/or pruritus of the skin and/or of the mucous membranes.

The present invention therefore more particularly features the formulation of at least one salt selected from among lanthanide, manganese, tin or yttrium salts into a cosmetic, dermatological or pharmaceutical composition, such compositions being intended for treating sensitive skins.

The present invention more particularly features the formulation of at least one salt selected from among lanthanide, manganese, tin or yttrium salts into a cosmetic or dermatological or pharmaceutical composition, such compositions being used for preventing and/or combating skin irritations and/or sores and/or erythemas and/or sensations of inflammation and/or dysaesthesia and/or pruritus of the skin and/or the mucous membranes.

Exemplary such salts include carbonates, bicarbonates, sulfates, glycerophosphates, borates, chlorides, nitrates, acetates, hydroxides, persulfates as well as salts of α-hydroxy acids (citrates, tartrates, lactates, malates) or of the fruit acids in general, or, alternatively, salts of amino acids (aspartate, arginate, glycocholate, fumarate) or salts of fatty acids (palmitate, oleate, caseinate, behenate).

Preferably, the salts are chlorides or nitrates, advantageously of neodymium, gadolinium or yttrium.

According to the present invention, the salt is advantageously formulated in an amount ranging from $10^{-5}\%$ to 20% of the total weight of the composition and, preferably, in an amount ranging from $10^{-2}\%$ to 15% of the total weight of the composition and, more preferably, from 0.5% to 8% of the total weight of the composition.

The salt can be formulated into a composition which must be ingested, injected or topically applied onto the skin (on any area of skin of the body), the hair, the nails or the mucous membranes (buccal, jugal, gingival, genital, anal, nasal, conjunctival). Depending on the mode of administration, this composition can be provided in any of the pharmaceutical dosage forms normally employed.

For topical application onto the skin, the composition may have the form, especially, of an aqueous, aqueous-alcoholic or oily solution, or of an oily suspension, or of a dispersion of the lotion or serum type, of emulsions of liquid or semi-liquid consistency of the milk type, which are obtained by dispersing a fatty phase in an aqueous phase (O/W) or, conversely, (W/O), or of suspensions or emulsions of soft consistency of the cream type or of aqueous or anhydrous gels, of micro-emulsions or, alternatively, microcapsules or microparticles, or of vesicular dispersions of the ionic and/or nonionic type. These compositions are formulated via the usual techniques.

They may also be applied to the hair in the form of aqueous, alcoholic or aqueous-alcoholic solutions, or in the form of creams, gels, emulsions or foams.

For injection, the composition may be provided in the form of an aqueous lotion, an oily suspension, or in the form of a serum. For the eyes, it may be provided in the form of drops and, for ingestion, it may be provided in the form of capsules, granules, syrups or tablets.

The amounts of the various constituents of the compositions according to the invention are those conventionally used in the fields under consideration.

These compositions constitute, in particular, cleansing, protecting, treatment or care creams for the face, for the hands, for the feet, for large anatomical folds or for the body (for example day creams, night creams, makeup removing creams, foundation creams, antisun or sunscreen creams), fluid foundations, makeup removing milks, body protecting or care milks, aftersun milks, lotions, gels or foams for skin care, such as cleansing lotions, aftersun lotions, artificial tanning lotions, bath compositions, deodorant compositions comprising a bactericidal agent, aftershave gels or lotions, depilatory creams, compositions against insect bites, antipain compositions, compositions for treating certain skin diseases such as eczema, rosasea, psoriasis, lichens, severe pruritus and those indicated above.

The compositions according to the invention may also comprise solid preparations, e.g., cleansing bars or soaps.

The subject compositions may also be packaged in the form of an aerosol composition, also comprising a pressurized propellent agent.

The salt according to the invention may also be incorporated into various compositions for hair care, and especially shampoos, hairsetting lotions, treatment lotions, hair-styling creams or gels, dye compositions (especially oxidation dyes) optionally in the form of coloring shampoos, restructuring lotions for the hair, permanent-waving compositions (especially compositions for the first stage of a permanent waving), lotions or gels for preventing hair loss, antiparasitic shampoos and the like.

The compositions may also be for dentibuccal or oral use, for example a toothpaste. In this case, the compositions may contain customary adjuvants and additives for compositions suited for oral use and, especially, surface-active agents, thickening agents, humectants, polishing agents such as silica, various active ingredients such as fluorides, in particular sodium fluoride and optionally sweeteners such as sodium saccharinate.

When the composition is an emulsion, the proportion of fatty phase may range from 5% to 80% by weight, and preferably from 5% to 50% by weight relative to the total weight of the composition. The oils, waxes, emulsifiers and coemulsifiers used in the compositions in the form of an emulsion are selected from among those conventionally used in the cosmetics field. The emulsifier and the coemulsifier are present in the composition in a proportion advantageously ranging from 0.3% to 30% by weight, preferably from 0.5% to 20% by weight relative to the total weight of the composition. The emulsion may, in addition, contain lipid vesicles.

When the composition is an oily gel or solution, the fatty phase may constitute more than 90% of the total weight of the composition.

In known manner, the pharmaceutical composition may also contain adjuvants and additives normally used in the pharmaceutical field, such as hydrophilic or lipophilic gelling agents, hydrophilic or lipophilic additives, preservatives, antioxidants, solvents, perfumes, fillers, sunscreens, odor absorbers and colorants. The amounts of these various adjuvants and additives are those conventionally used in the cosmetics field, and range, for example, from 0.01% to 20% of the total weight of the composition. These adjuvants and additives, depending on their nature, may be introduced into the fatty phase, into the aqueous phase and/or into the lipid spherules.

Exemplary oils or waxes according to the invention include mineral oils, vegetable oils (soya bean oil, palm oil, liquid fraction of shea butter, sunflower oil), animal oils (perhydrosqualene), synthetic oils, silicone oils or waxes (cyclomethicone, dimethicone) and fluorinated oils (perfluoropolyethers). Fatty alcohols (cetyl alcohol), fatty acids (stearic acid) and waxes (beeswax, carnauba wax and paraffin wax) may be added to these oils.

Exemplary emulsifiers which are suitable according to the invention include glycerol stearate, PEG-100 stearate, polyglyceryl-3 hydroxylauryl ether and polysorbate 60.

Exemplary solvents which are suitable include the lower alcohols, especially ethanol and isopropanol, and propyleneglycol.

Exemplary hydrophilic gelling agents according to the invention include carboxyvinyl polymers (carbomer), acrylic copolymers such as acrylate/alkylacrylate copolymers, polyacrylamides, polysaccharides such as hydroxypropyl-cellulose, natural gums and clays. And exemplary lipophilic gelling agents include modified clays such as bentones, metallic salts of fatty acids such as aluminum stearates and hydrophobic silica, ethyl cellulose, and polyethylene.

The subject compositions may contain other hydrophilic active agents, such as proteins or protein hydrolysates, amino acids, polyols, urea, allantoin, sugars and sugar derivatives, water-soluble vitamins, vegetable or bacteria extracts and starch.

Representative lipophilic active agents include retinol (vitamin A) and derivatives thereof, tocopherol (vitamin E) and derivatives thereof, essential fatty acids, ceramides, essential oils.

According to this invention, it is envisaged to combine, inter alia, with the lanthanide, manganese, tin or yttrium salts, other active agents suited, especially, for the prevention and/or treatment of skin conditions/afflictions.

Exemplary active agents include:
(1) skin pigmentation and/or proliferation and/or differentiation modulating agents, such as retinoic acid and isomers thereof, retinol and esters thereof, vitamin D and derivatives thereof, estrogens such as estradiol, kojic acid or hydroquinone;
(2) antibacterial agents such as clindamycin phosphate, erythromycin or antibiotics of the tetracycline class;
(3) antiparasitic agents, in particular metronidazole, crotamiton or pyrethrinoids;

(4) antifungal agents, in particular the compounds belonging to the imidazole class such as econozale, ketoconazole or miconazole or salts thereof, polyene compounds such as amphotericin B, compounds of the allylamine family, such as terbinafine, or alternatively octopirox;

(5) antiviral agents such as acyclovir;

(6) steroidal anti-inflammatory agents such as hydrocortisone, betamethasone valerate or clobetasol propionate, or nonsteroidal anti-inflammatory agents such as ibuprofen and salts thereof, diclofenac and salts thereof, acetylsalicylic acid, acetaminophen or glycyrrhetinic acid;

(7) anaesthetic agents such as lidocaine hydrochloride and derivatives thereof;

(8) antipruritic agents such as thenaldine, trimeprazine or cyproheptadine;

(9) keratolytic agents such as alpha- and beta-hydroxycarboxylic or -ketocarboxylic acids, their salts, amides or esters and, more particularly, hydroxy acids such as glycolic acid, lactic acid, salicylic acid, citric acid and, in general, fruit acids, and n-octanoyl-5-salicylic acid;

(10) anti-free radical agents such as alpha-tocopherol or esters thereof, superoxide dismutases, certain metal chelators or ascorbic acid and esters thereof;

(11) antiseborrhoeic agents such as progesterone;

(12) antidandruff agents such as octopirox or zinc pyrithione;

(13) antiacne agents such as retinoic acid or benzoyl peroxide;

(14) antiseptics;

(15) antimetabolites;

(16) agents for combating hair loss, such as minoxidil.

Thus, in a specific embodiment of the invention, the subject compositions comprise at least one salt selected from among lanthanide, manganese, tin and yttrium salts and at least one active agent selected from among antibacterial, antiparasitic, antifungal, antiviral, anti-inflammatory, antipruritic, anaesthetic, keratolytic, anti-free radical, antiseborrhoeic, antidandruff, or anti-acne agents and/or skin pigmentation and/or proliferation and/or differentiation modulating agents.

Advantageously, at least one lanthanide, manganese, tin or yttrium salt is combined with products or species eliciting an irritant effect and which are commonly used in the cosmetic, dermatological or pharmaceutical field, agents which are sometimes cosmetic, dermatological or pharmaceutical active principles. The presence of a substance P antagonist in the form of at least one lanthanide, manganese, tin or yttrium salt in a cosmetic, dermatological or pharmaceutical composition comprising an active agent eliciting an irritant effect makes it possible to attenuate substantially, or even suppress or eliminate, this irritant effect. This additionally permits increasing the amount of active agent eliciting an irritant effect relative to the amount of active agent normally used, for enhanced efficacy.

Thus, this invention also features cosmetic, dermatological or pharmaceutical compositions comprising, in a cosmetically, dermatologically or pharmaceutically acceptable medium (vehicle, diluent or carrier), at least one active species eliciting an irritant effect, and further comprising at least one salt selected from among lanthanide, manganese, tin and yttrium salts and a mixture thereof, and preferably a neodymium or yttrium salt.

Exemplary active agents eliciting an irritant effect include surfactants (ionic or nonionic), preservatives, organic solvents or active agents such as α-hydroxy acids (citric, malic, glycolic, tartaric, mandelic or lactic acid), β-hydroxy acids (salicylic acid and its derivatives), α-keto acids, β-keto acids, retinoids (retinol, retinal retinoid acid), anthralins (dioxyanthranol), anthranoids, peroxides (especially of benzoyl), minoxidil, lithium salts, antimetabolites, vitamin D and derivatives thereof, hair dyes or colorants (para-phenylenediamine and derivatives thereof, aminophenols), perfuming alcoholic solutions (perfumes, toilet water, aftershave, deodorants), antiperspirants (certain aluminum salts), depilatory or permanent-waving active agents (thiols), depigmenting active agents (hydroquinone).

The incorporation of a substance P antagonist makes it possible, in particular, to multiply by 2 to 10 times the amount of active agent eliciting an irritant effect compared to the state of the art, without experiencing any of the discomforts mentioned above. Thus, the hydroxy acids may be incorporated up to 50% of the weight of the composition, or the retinoids up to 5%, while significantly reducing their irritant effect.

The compositions according to the invention comprising, in a cosmetically, dermatologically or pharmaceutically acceptable medium, at least one species eliciting an irritant effect and at least one salt selected from among lanthanide, manganese, tin, and yttrium salts and a mixture thereof can very obviously be formulated in any known pharmaceutical or cosmetic dosage form, such as, in particular, those described above.

Moreover, the salts of the invention can be combined with CGRP (Calcitonin Gene Related Peptide or peptide linked to the calcitonin gene) antagonists, for example, extracts of Iridaceae such as *Iris pallida*, substance P antagonists as described in published FR-94 05537, assigned to the assignee hereof, or strontium salts, and antagonists of histamine, interleukin-1 and/or TNF-α (Tumour Necrosis Factor-alpha).

The present invention also features a cosmetic, dermatological or pharmaceutical treatment regimen, especially for reducing the irritant effect of a cosmetic, dermatological or pharmaceutical composition or for treating sensitive skins, according to which a composition as described above is topically applied onto the skin, onto the hair and/or onto the mucous membranes.

These treatments are advantageously carried out by applying the hygienic, cosmetic or pharmaceutical compositions described above according to the usual techniques. For example: application of creams, gels, serums, lotions, makeup removing milks or aftersun or sunscreen compositions onto the skin or onto dry hair, application of a hair lotion onto wet hair, of shampoos, or application of toothpaste onto the gums.

In order to further illustrate the present invention and the advantages thereof, the following specific examples are given, it being understood that same are intended only as illustrative and in nowise limitative.

In said examples to follow, all parts and percentages are given by weight, unless otherwise indicated.

EXAMPLE 1

| Cleansing cream (Formula A): | |
|---|---|
| Yttrium carbonate | 5.00 |
| Cetyl alcohol | 2.00 |
| Glycerol stearate | 2.00 |
| Stearic acid | 2.00 |
| Polyglyceryl-3 Hydroxylauryl Ether | 5.00 |
| Mineral oil Codex | 12.00 |
| Carbomer | 0.35 |
| Sodium hydroxide | 0.15 |
| Perfume | qs |

EXAMPLE 2

Cleansing milk (Formula B):

| | | |
|---|---|---|
| Lanthanum nitrate | | 0.5 |
| Carbomer | | 0.40 |
| Sodium hydroxide | | 0.10 |
| Mineral oil Codex | | 5.00 |
| Glycerol stearate | | 1.00 |
| Cetyl alcohol | | 0.50 |
| PEG 100 stearate | | 0.80 |
| Methyl paraben | | 0.20 |
| Perfume | qs | |
| Sterile demineralized water | qs | 100.00 |

EXAMPLE 3

Care lotion (Formula C):

| | | |
|---|---|---|
| Manganese chloride | | 15.00 |
| Glycerol | | 2.00 |
| Methyl paraben | | 0.15 |
| Perfume | qs | |
| Sterile demineralized water | qs | 100.00 |

EXAMPLE 4

Care cream (Formula D):

| | | |
|---|---|---|
| Europium chloride | | 1.00 |
| Glycerol stearate | | 1.00 |
| PEG 100 stearate | | 1.00 |
| Stearic acid | | 1.00 |
| Cetyl alcohol | | 2.00 |
| Soya bean oil | | 3.00 |
| Palm oil | | 2.00 |
| Cyclomethicone | | 2.00 |
| Dimethicone | | 1.00 |
| Polyacrylamide | | 0.20 |
| Glycerol | | 3.00 |
| Methyl paraben | | 0.20 |
| Perfume | qs | |
| Sterile demineralized water | qs | 100.00 |

EXAMPLE 5

Makeup removing lotion for the face (Formula E):

| | | |
|---|---|---|
| Neodymium citrate | | 0.5 |
| Antioxidant | | 0.05 |
| Isopropanol | | 40.00 |
| Preservative | | 0.30 |
| Water | qs | 100% |

EXAMPLE 6

Face care gel (Formula F):

| | | |
|---|---|---|
| Holmium chloride | | 0.5 |
| Hydroxypropylcellulose (Klucel H marketed by Hercules) | | 1.00 |
| Antioxidant | | 0.05 |
| Isopropanol | | 40.00 |
| Preservative | | 0.30 |
| Water | qs | 100% |

EXAMPLE 7

Care cream for solar erythema (oil-in-water emulsion) (Formula G):

| | | |
|---|---|---|
| Neodymium chloride | | 5.00 |
| Glycerol stearate | | 2.00 |
| Polysorbate 60 (Tween 60 marketed by the company ICI) | | 1.00 |
| Stearic acid | | 1.40 |
| Glycyrrhetinic acid | | 2.00 |
| Triethanolamine | | 0.70 |
| Carbomer | | 0.40 |
| Liquid fraction of shea butter | | 12.00 |
| Sunflower oil | | 10.00 |
| Antioxidant | | 0.05 |
| Perfume | | 0.5 |
| Preservative | | 0.30 |
| Water | qs | 100% |

The following examples are of formulations illustrating the invention and particularly compositions comprising at least one lanthanide, manganese, tin or yttrium salt and an active species normally eliciting an irritant effect. These compositions were formulated simply by mixing the various components.

EXAMPLE 8

Composition 1: Gel for the treatment of acne:

| | | |
|---|---|---|
| Manganese borate | | 5.00 |
| All-trans-retinoid acid | | 0.05 |
| Hydroxypropylcellulose (Klucel H) | | 1.00 |
| Antioxidant | | 0.05 |
| Isopropanol | | 40.00 |
| Preservative | | 0.30 |
| Water | qs | 100% |

EXAMPLE 9

Composition 2: Lotion for removing scars due to acne:

| | | |
|---|---|---|
| Neodymium chloride | | 1.5 |
| Glycolic acid | | 50.00 |
| Hydroxypropylcellulose (Klucel H) | | 0.05 |
| NaOH | qs pH = | 2.80 |
| Ethanol | qs | 100% |
| Preservative | | 0.30 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for the treatment of a mammalian disorder, a manifestation of which is selected from the group consisting of (i) an excess in the synthesis of substance P, (ii) an excess in the release of substance P, and (iii) an excess in both the synthesis and release of substance P comprising administering to a mammalian organism in need of such treatment an effective substance P antagonist amount of at least one salt of yttrium, lanthanum, cerium, praseodymium, neodymium, promethium, samarium, europium, gadolinium, terbium, dysprosium, holmium, erbium, thulium, ytterbium, lutetium, tin, manganese, or mixture thereof.

2. The method as defined by claim 1, comprising topically applying said at least one salt onto at least one of the skin, the hair, or the mucous membranes of said mammalian organism.

3. The method as defined by claim 1, wherein said mammalian disorder is selected from the group consisting of a disorder of the central nervous system, a respiratory disorder, an allergic syndrome, inflammation, pain, a gastrointestinal disorder, a skin disorder, fibroses, a collagen-maturation disorder, a cardiovascular disorder, a vasospastic disorder, an immunological disorder, a disorder of the urogenital tract, an ophthalmic and a pancreatic disorder.

4. The method as defined by claim 1, wherein said mammalian disorder is a cutaneous disorder.

5. The method as defined by claim 1, wherein said mammalian disorder comprises sensitive skin.

6. The method as defined by claim 1, which is used to treat at least one condition selected from the group consisting of cutaneous irritations, sores, erythemas, dysaesthetic sensations, warming sensations, pruritus of the skin, or pruritus of the mucous membranes.

7. The method as defined by claim 1, wherein said at least one salt is selected from the group consisting of a salt of neodymium, gadolinium, yttrium, and combinations thereof.

8. The method as defined by claim 1, wherein said at least one salt is selected from the group consisting of a chloride, borate, bicarbonate, carbonate, nitrate, hydroxide, sulfate, glycerophosphate, a salt of a fruit acid and a salt of an amino acid.

9. The method as defined by claim 8, wherein said at least one salt is a chloride or nitrate.

10. The method as defined by claim 1, comprising coadministering to said mammalian organism in combination with said substance P antagonist salt at least one other agent selected from the group consisting of (i) at least one antibacterial active agent, (ii) at least one active agent for combating parasites, (iii) at least one antifungal active agent, (iv) at least one antiviral active agent, at least one anti-inflammatory active agent, (v) at least one antipruriginous active agent, (vi) at least one anaesthetic active agent, (vii) at least one keratolytic active agent, (viii) at least one active agent for combating free radicals, (ix) at least one antiseborrhoiec active agent, (x) at least one antidandruff active agent, (xi) at least one antiacne active agents, (xii) at least one active agent which modulates cutaneous pigmentation (xiii) at least one active agent which modulates cutaneous proliferation and (xiv) at least one active agent which modulates cutaneous differentiation.

11. A cosmetic or pharmaceutical composition of matter suited for the treatment of a mammalian disorder, a manifestation of which is selected from the group consisting of (i) an excess in the synthesis of substance P (ii) an excess in the release of substance P, and (iii) an excess in the synthesis and release of substance P comprising an effective substance P antagonist amount of at least one salt selected from the group consisting of yttrium, cerium, praseodymium, neodymium, promethium, samarium, europium, gadolinium, terbium, dysprosium, holmium, erbium, thulium, ytterbium, lutetium, tin, manganese, and combinations thereof, contained in a cosmetically/pharmaceutically acceptable medium thereof.

12. The cosmetic or pharmaceutical composition as defined by claim 11, which is suitable for topical application.

13. The cosmetic or pharmaceutical composition as defined by claim 11, wherein said at least one salt comprises from $10^{-5}\%$ to 20% of the total weight thereof.

14. The cosmetic or pharmaceutical composition as defined by claim 13, wherein said at least one salt comprises from $10^{-2}\%$ to 15% of the total weight thereof.

15. The cosmetic or pharmaceutical composition as defined by claim 11, further comprising a normally skin-irritating amount of at least one skin irritant.

16. The cosmetic or pharmaceutical composition as defined by claim 11, further comprising at least one other antagonist selected from the group consisting of CGRP antagonist, histamine antagonist, interleukin-1 antagonist, TNF antagonist, and a different substance P antagonist than said at least one substance P antagonist salt.

17. The cosmetic or pharmaceutical composition as defined by claim 15, wherein said at least one skin irritant is selected from the group consisting of a surfactant, preservative, organic solvent, α-hydroxy acid, β-hydroxy acid, α-keto acid, β-keto acid, retinoid, anthralin, anthranoid, peroxide, minoxidil, lithium salt, antimetabolite, vitamin D, vitamin D derivative, hair dye, hair colorant, alcoholic perfume, antiperspirant, depilatory, permanent-wave, depigmenting active agent, and combinations thereof.

18. The cosmetic or pharmaceutical composition as defined by claim 11, further comprising an effective amount of at least one additional agent selected from the group consisting of at least one antibacterial active agent, at least one active agent for combating parasites, at least one antifungal active agent, at least one antiviral active agent, at least one anti-inflammatory active agent, at least one antipruriginous active agent, at least one anaesthetic active agent, at least one keratolytic active agent, at least one active agent for combating free radicals, at least one antiseborrhoeic active agent, at least one antidandruff active agent, at least one antiacne active agent, at least one active agent which modulates cutaneous pigmentation, at least one active agent which modulates cutaneous proliferation and at least one active agent which modulates cutaneous differentiation.

19. The cosmetic or pharmaceutical composition as defined by claim 11, which is in a form selected from the group consisting of a lotion, suspension, serum, eyedrops, capsules, granules, syrup, tablets, emulsion, milk, cream, gel, microcapsules, microparticles, vesicular dispersion, solution, foam, aerosol, cleansing bar, soap, toothpaste, shampoo, and hair care formulation.

* * * * *

UNITED STATES PATENT AND TRADEMARK OFFICE
CERTIFICATE OF CORRECTION

PATENT NO. : 5,900,257
DATED : May 4, 1999
INVENTOR(S) : Breton et al

It is certified that error appears in the above-identified patent and that said Letters Patent is hereby corrected as shown below:

On the Title Page:

Item [45], please delete "Date of Patent: May 5, 1999", and replace with --Date of Patent: May 4, 1999--.

Signed and Sealed this

Twenty-seventh Day of March, 2001

Attest:

NICHOLAS P. GODICI

Attesting Officer

Acting Director of the United States Patent and Trademark Office